(12) United States Patent
Pouet

(10) Patent No.: US 7,978,341 B2
(45) Date of Patent: Jul. 12, 2011

(54) MULTI-CHANNEL LASER INTERFEROMETRIC METHOD AND APPARATUS FOR DETECTION OF ULTRASONIC MOTION FROM A SURFACE

(75) Inventor: Bruno Francois Pouet, Los Angeles, CA (US)

(73) Assignee: Bossa Nova Technologies, LLC, Venice, CA (US)

( * ) Notice: Subject to any disclaimer, the term of this patent is extended or adjusted under 35 U.S.C. 154(b) by 750 days.

(21) Appl. No.: 10/583,954

(22) PCT Filed: Dec. 22, 2004

(86) PCT No.: PCT/US2004/043378
§ 371 (c)(1),
(2), (4) Date: Aug. 19, 2008

(87) PCT Pub. No.: WO2005/062941
PCT Pub. Date: Jul. 14, 2005

(65) Prior Publication Data
US 2009/0027688 A1    Jan. 29, 2009

Related U.S. Application Data

(60) Provisional application No. 60/531,147, filed on Dec. 22, 2003.

(51) Int. Cl.
*G01B 11/02* (2006.01)
(52) U.S. Cl. ........................................ 356/502
(58) Field of Classification Search .................. 356/502
See application file for complete search history.

(56) References Cited

U.S. PATENT DOCUMENTS

| | | | | |
|---|---|---|---|---|
| 4,121,470 | A * | 10/1978 | Kaule | 73/643 |
| 5,212,667 | A * | 5/1993 | Tomlinson et al. | 367/7 |
| 5,402,235 | A * | 3/1995 | Monchalin | 356/502 |
| 5,546,187 | A * | 8/1996 | Pepper et al. | 356/487 |
| 6,075,603 | A * | 6/2000 | O'Meara et al. | 356/496 |
| 6,128,092 | A | 10/2000 | Levesque et al. | |
| 6,847,454 | B2 * | 1/2005 | Crowley et al. | 356/479 |
| 7,006,231 | B2 * | 2/2006 | Ostrovsky et al. | 356/479 |
| 7,130,054 | B2 * | 10/2006 | Ostrovsky et al. | 356/479 |
| 7,426,037 | B2 * | 9/2008 | Ostrovsky et al. | 356/479 |
| 7,728,983 | B2 * | 6/2010 | Ostrovsky et al. | 356/479 |
| 2003/0020922 | A1 * | 1/2003 | Crowley et al. | 356/502 |
| 2005/0099634 | A1 * | 5/2005 | Dubois et al. | 356/502 |
| 2005/0264826 | A1 * | 12/2005 | Ostrovsky et al. | 356/502 |
| 2006/0262319 | A1 * | 11/2006 | Gatt | 356/492 |
| 2009/0122322 | A1 * | 5/2009 | Pouet | 356/497 |

OTHER PUBLICATIONS

International Search Report for PCT/US2004/43378 dated Jun. 27, 2005 (1 page).

* cited by examiner

*Primary Examiner* — Patrick J Connolly
(74) *Attorney, Agent, or Firm* — Osha • Liang LLP

(57) ABSTRACT

A multi-channel laser interferometric method and apparatus are provided for optically measuring transient motion from a surface (17). A laser beam (11) is generated and then divided into first and second beams having respective intensities representing minor and major fraction of the predetermined laser intensity. The reference beam (18) illuminates the surface (17) at which deformation is expected. The light back-scattered by the surface is collected by a single aperture lens (15) and then made to interfere with the probe beam (67) which has been expanded (32), onto a two-dimensional array of detectors (71). Each signal (83) corresponding to each detector of the array is converted individually to an electrical signal, each electrical signal is amplified and processed (84), and the plurality of processed signals (85) is then averaged in an electrical summing means (45).

21 Claims, 14 Drawing Sheets

MULTI-CHANNEL LASER INTERFEROMETRIC METHOD AND APPARATUS FOR DETECTION OF ULTRASONIC MOTION FROM A SURFACE

BACKGROUND OF INVENTION

The present invention relates to laser interferometric method and apparatus with large collecting aperture for measuring motion from a surface. The invention is particularly directed toward detecting small displacement of a surface, and more particularly, an optically scattering surface, of a workpiece subjected to ultrasound, where the workpiece does not need to be accurately positioned.

The detection of phase modulation of an optical wave is important for various field of application where optical beams are used to detect the small motion of an object. This is the case of laser detection of ultrasound and transient body motion such as those produced by the sudden absorption of a laser pulse. The technique based on laser generation and detection, known as Laser Ultrasonic (LU) or Laser Based Ultrasonic (LUB), allows for remote and non-contact detection and generation of ultrasound. Laser ultrasonics can thus be advantageously used for inspection at high temperature, on-line and during process. Most of the industrial application of laser ultrasonics involves the inspection of an "optically rough" surface. The probed surfaces being optically rough, the ultrasonic information is thus encoded in an optical beam with speckle. A suitable interferometric technique should integrate effectively over the large speckle field and provide an output signal independently of the speckle nature the collected light. Adequate sensitivity requires an interferometric technique which has a large effective light gathering efficiency. Interferometric techniques based on plane wave reference using heterodyne scheme (U.S. Pat. No. 4,633,715) or quadrature scheme (U.S. Pat. No. 5,404,224) are only effective if the two interfering beams (the reference beam and the object beam reflected from the sample) are plane waves. For object with rough surfaces reflecting a speckled beam, the plane-wave interference requirement means that only a single speckle should be selected from the object beam for high efficiency interference. Single speckle selection means that the collecting aperture is very small and thus these interferometers have very low sensitivity on rough surfaces. Instead of single speckle detection, these interferometers can be optimized for collecting few speckles in order to increase the amount of collected light, but unfortunately the sensitivity is not directly improved by the higher amount of collected light because the random phase distribution of speckles reduces the interference efficiency.

In various U.S. patents, laser interferometric schemes for detection on rough surfaces have been described. These schemes are characterized by their large étendue parameter. These laser interferometric schemes are based on confocal Fabry-Pérot (U.S. Pat. No. 4,966,459) or adaptive photorefractive interferometer (U.S. Pat. No. 5,131,748)

For industrial application, the reduction in the need for accurate object positioning is as critical as to have a high sensitivity on a rough surface. In most industrial application, the positioning of the sample is not controlled accurately. An optical system with high sensitivity but high requirement for target positioning will lead to an overall system with poor sensitivity, where good signals are acquired only sporadically when the sample moves through the optimum position. To better control the sample position may not be easily possible or may highly increase the overall cost of the inspection system, making the system not affordable and limiting its field of application. Often a compromised is used by detuning the system in order to get more uniform performance over a larger range of sample positions, at the expense of the maximum sensitivity.

Accordingly, it is one of the principle objects of the invention to provide a method and apparatus for optically detecting ultrasonic transient motion from scattering surface, having a high sensitivity, a large gathering optics as well as a large depth-of-field. The depth-of-field (DOF) is defined as the variation in the stand-off distance that causes a reduction by a factor two from the maximum sensitivity of the optical system.

SUMMARY OF INVENTION

In accordance with a first aspect of the invention, there is thus provided a multi-channel laser interferometric method for measuring the displacement of a surface of a material subjected to ultrasound, which comprises:

generating a laser beam having a predetermined intensity;

dividing the laser beam into a reference beam and a probe beam having respective intensities representing minor and major fractions of the predetermined intensity;

passing the probe beam through an optical lens to focalize the probe beam onto the surface of the material subjected to ultrasound, thereby scattering same;

expanding the reference beam;

combining the scattered probe beam collected by said optical lens with said expanded reference beam to obtain an optical fringe signal;

receiving said optical fringe signal on at least one array of photodetectors, wherein said optical fringe signal fully covers said array and each photodetector of the array defines a channel, having a given aperture smaller than the aperture of said optical lens to receive a portion of said optical fringe signal and converting said portion of said optical fringe signal into an electrical signal;

processing for each channel said electrical signals through circuitry means;

summing electrically said processed signals to extract an output signal correlated to the motion of said surface.

According to a first embodiment, processing comprises first filtering the electrical signals, then squaring the filtered signals.

According to a second embodiment, processing comprises first filtering the electrical signals, then rectifying the filtered signals.

According to a further embodiment of the method, it further comprises linearly polarizing the scattered probe beam collected by the optical lens, circularly polarizing the expanded reference beam, combining the linearly polarized scattered probe beam with the circularly polarized expanded reference beam to obtain two optical fringe signals having a phase shift of 90° and receiving the first and second optical fringe signals on two arrays of detectors, the two arrays of detectors being identical, two detectors of the corresponding channels of the arrays generating two in-quadrature electrical signals, the electrical signal pairs being then processed together through the circuitry means.

According to a first embodiment, the step of processing comprises first dividing and filtering the in-quadrature signal pairs to separate each signal into a high-frequency signal and a low-frequency signal, then for each signal pair, generating two signals by cross-multiplication between the low-frequency signal pair and the high-frequency signal pair, and differentiating the two signals.

According to a second embodiment, the step of processing comprises first dividing and processing the in-quadrature signal pairs to separate each signal into the original signal and its derivative signal, then for each signal pair, generating two signals by cross-multiplication between the original signal pair and the derivative signal pair, and differentiating the two signals.

According to a third embodiment, the step of processing comprises first high-pass filtering the signal pairs, then for each signal pair, sunning the two signals obtained by squaring of each signal of the signal pair.

According to a quarter embodiment, the step of processing comprises first high-pass filtering the signal pairs, then for each signal pair, summing the two signals obtained by rectification of each signal of the signal pair.

According to a further embodiment of the method, the scattered probe beam and the expanded reference beam have crossed polarization, and it further comprises dividing each of the scattered probe beam and the expanded reference beam in two optical signals having a 180° phase difference, the combining of the optical signals resulting in four optical fringe signals having −90°, 0°, 90° and 180° relative phase differences; the step of receiving further comprises:
  receiving the four optical fringe signals on four arrays of detectors, the four arrays of detectors being identical, each set of four detectors of a corresponding channel generating two in-quadrature pairs of out-of-phase electrical signals,
  subtracting each out-of-phase electrical signals to obtain a pair of differential in-quadrature electrical signals for each channel, the pairs of differential in-quadrature electrical signals being processed together through the circuitry means.

According to a further embodiment of the method, it further comprises frequency shifting the reference beam, the optical fringe signal resulting from combining the scattered probe beam with the expanded shifted reference beam being an heterodyne optical fringe signal; and the step of processing comprises demodulating each electrical signal for each channel by removing the frequency shift using heterodyne demodulation techniques.

In accordance with a second aspect of the invention, there is provided a multi-channel laser interferometric apparatus for measuring the motion of a surface of a material subjected to ultrasound, which comprises:
  a laser source for generating a laser beam having a predetermined intensity;
  a beam splitter for dividing said laser beam into a reference beam and a probe beam having respective intensities representing minor and major fractions of said predetermined intensity;
  an optical lens disposed for focalizing said probe beam onto the surface of said material subjected to ultrasound, thereby scattering same;
  a beam expander expanding said reference beam;
  combining means for combining the scattered probe beam with said expanded reference beam to obtain an optical fringe signal;
  receiving means with at least one array of detectors for receiving said optical fringe signal on, wherein the optical fringe signal fully covers the array, and each detector, defining a channel, has a given aperture smaller than the aperture of said optical lens to receive a portion of said optical fringe signal and convert said portion of said optical fringe signal into an electrical signal;
  circuitry means for processing for each channel said electrical signals and summing said processed signals to extract an output signal correlated to motion of the surface.

According to a first embodiment, the array of detectors is a linear array of detectors.

According to a second embodiment, the array of detectors is a two-dimensional array of detectors According to a third embodiment, circuitry means comprise filtering means for filtering the electrical signals and squaring means for squaring the filtered signals.

According to a quarter embodiment, circuitry means comprise filtering means for filtering the electrical signals and rectifying means for rectifying the filtered signals.

According to a further embodiment, the apparatus further comprises polarizing means for circularly polarizing the expanded reference beam, and the combining means comprise a polarizing beam splitter for combining the linearly polarized scattered probe beam with the expanded circularly polarized reference beam to obtain two optical fringe signals having a phase shift of 90°; the receiving means comprise two identical arrays of detectors for receiving the optical fringe signals on, the two detectors of a same channel of each array generating a pair of in-quadrature electrical signals, the pairs of in-quadrature electrical signals being then processed together by the circuitry means.

According to a further embodiment, the apparatus further comprises polarizing means for setting the polarization of the expanded reference beam orthogonal to the polarization of the probe beam; dividing means to divide each of the polarized scattered probe beam and the expanded orthogonally polarized reference beam into a first and a second signals; an optical retardation device in one of the first or second optical signals to obtain a phase shift of 90° between the first and second optical signals; and the combining means comprise two polarized beam splitters for combining the two orthogonally polarized components of the first and second optical signals, each into two optical fringe signals having a 180° phase difference; resulting in four optical fringe signals having −90°, 0°, 90° and 180° relative phase differences; the receiving means comprise four identical arrays of detectors for receiving the four optical fringe signals, each set of four detectors of a corresponding channel generating two pairs of out-of-phase electrical signals; the circuitry means further comprise subtracting means for subtracting each of the out-of-phase electrical signals to obtain a pair of differential in-quadrature electrical signals for each said channel, the pairs of differential in-quadrature electrical signals being then processed together.

According to a further embodiment, the apparatus further comprises a frequency shifting device for frequency shifting the reference beam by a given frequency, the frequency shifted reference being then expended, and the combining means combine the scattered probe beam with the expanded frequency shifted reference beam to obtain an heterodyne optical fringe signal, the heterodyne optical fringe signal being received by the receiving means the circuitry means comprise demodulation means for processing for each channel the heterodyne electrical signals through demodulation by removing the frequency shift using standard heterodyne demodulation techniques, the output signal obtained by summing the processed signals being proportional to the displacement of the surface.

According to a further embodiment, the apparatus further comprises a multi-mode optical fiber and coupling means for coupling the laser beam into the optical fiber, and a partially reflecting coating at the optical fiber end enables dividing the laser beam into the reference beam and the probe beam; the optical lens for focalizing the probe beam onto the surface of the material is disposed at the end of the optical fiber, and refocuses the scattered probe beam into the optical fiber; the receiving means comprise at least one two-dimensional array of detectors and a second optical lens for focusing on the array of detectors the multi-mode optical beam exiting though the entrance face of the multi-mode fiber and corresponding to the mixing between the scattered beam and the partially reflected beam.

BRIEF DESCRIPTION OF DRAWINGS

Further features and advantages of the invention will become more readily apparent from the following description of preferred embodiments with reference to the appended drawings, in which.

DETAILED DESCRIPTION

Figure 1:
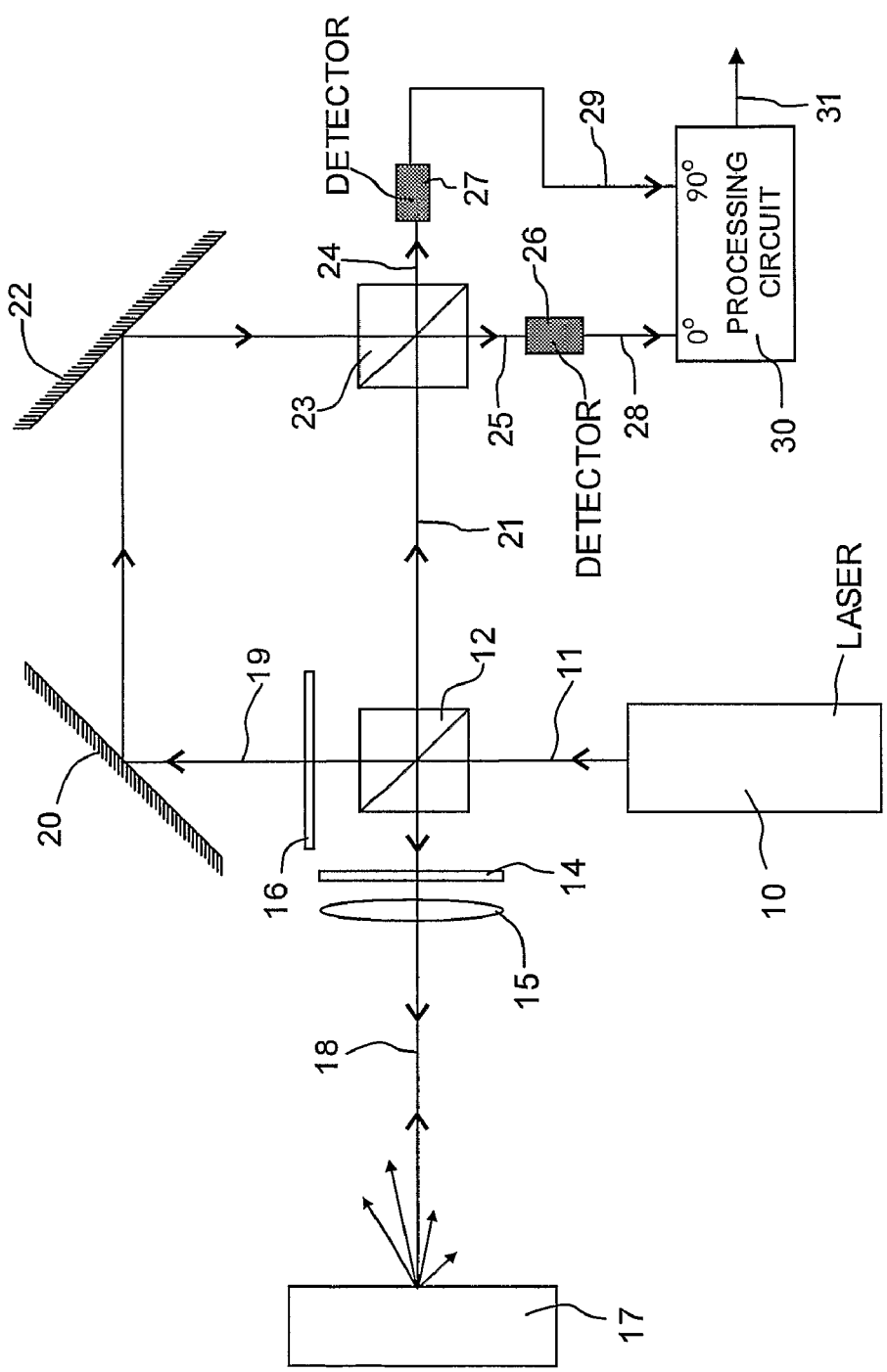
FIG. 1 is a schematic diagram of a Mach-Zehnder-type interferometric apparatus according to the prior art.

FIG. 1 schematically illustrates a Mach-Zehnder-type interferometric apparatus according to the prior art for measuring the displacement of a surface of a material subjected to ultrasound. A laser 10 is used to generate a laser beam 11. A polarizing beam splitter 12 is used to divide the laser beam 11 into a probe beam 18 and a reference beam 19 having respective intensities representing minor and major fractions of the intensity of the laser beam 11. The probe beam 18, reflected by the polarizing beam splitter 12, then passes through a quarter wave plate 14 whereby probe beam 18 is circularly polarized and focused by mean of a lens 15 onto the surface of a workpiece 17. The object beam 21, corresponding to the probe beam back-reflected by the workpiece and collected by the lens 15, is linearly polarized and is directed toward a polarizing beam splitter 23. The reference beam 19 passes a quarter wave plate 16 whereby reference beam is circularly polarized. The reference beam is picked-up by mirrors 20 and 22 and directed onto the polarizing beam splitter 23 which is set a 45° of the linear polarization axis of the object beam 21. The linearly polarized object beam 21 and the circularly polarized reference beam 19 are mixed and divided by the polarizing beam splitter 23 into two interference signals 24 and 25 which are detected by detectors 26 and 27. The electronic fringe signals 28 and 29 that are generated by the detectors exhibit a 90° phase difference. The quadrature signals are processed by a processing circuitry 30 to deliver an output signal 31 correlated to the motion of the surface. In this apparatus, a large collecting optical lens 15 enables to collect more scattered light and thus to enable an higher sensitivity of the measurement. But a large collecting optical system that relays the gathered light on a small size photodetector 26, 27, will quickly loose its gathering effectiveness when the interrogated surfaces moved away from the designed distance corresponding to the maximum light gathering. Furthermore, the collected scattered light is not efficiently used because of the random phase distributions of the speckles. Indeed, the gathering of large number of speckles on a single detector increases the average power collected but unfortunately it also averages out the phase information, strongly reducing its effectiveness.

Accordingly, it is one of the principle objects of the invention to provide a method and apparatus for optically detecting transient motion from scattering surface, having a large gathering optics, as well as a large depth-of-field. The interferometric apparatus according to the invention comprises a laser source for generating a laser beam having a predetermined intensity, a beam splitter for dividing the laser beam into a reference beam and a probe beam having respective intensities representing minor and major fractions of said predetermined intensity. It further comprises an optical lens disposed for focalizing the probe beam onto the surface of the material subjected to ultrasound, thereby scattering same, and a beam expander for expanding the reference beam. It also comprises combining means for combining the scattered probe beam with the expanded reference beam to obtain an optical fringe signal and receiving means with at least one array of detectors for receiving the optical fringe signal on, wherein the optical fringe signal fully covers the array. Each detector, defining a channel, has a given aperture smaller than the aperture of the optical lens to receive a portion of the optical fringe signal and convert this portion of the optical fringe signal into an electrical signal. It further comprises circuitry means for processing for each channel the electrical signals and summing the processed signals to extract an output signal correlated to motion of the surface.

The optical arrangement according to the invention thus implements a compact multi-channel interferometer that enables a large aperture interferometer. The signals of each interferometric channels are coherently added in order to generate the large aperture interferometric signal.

Figure 2A:
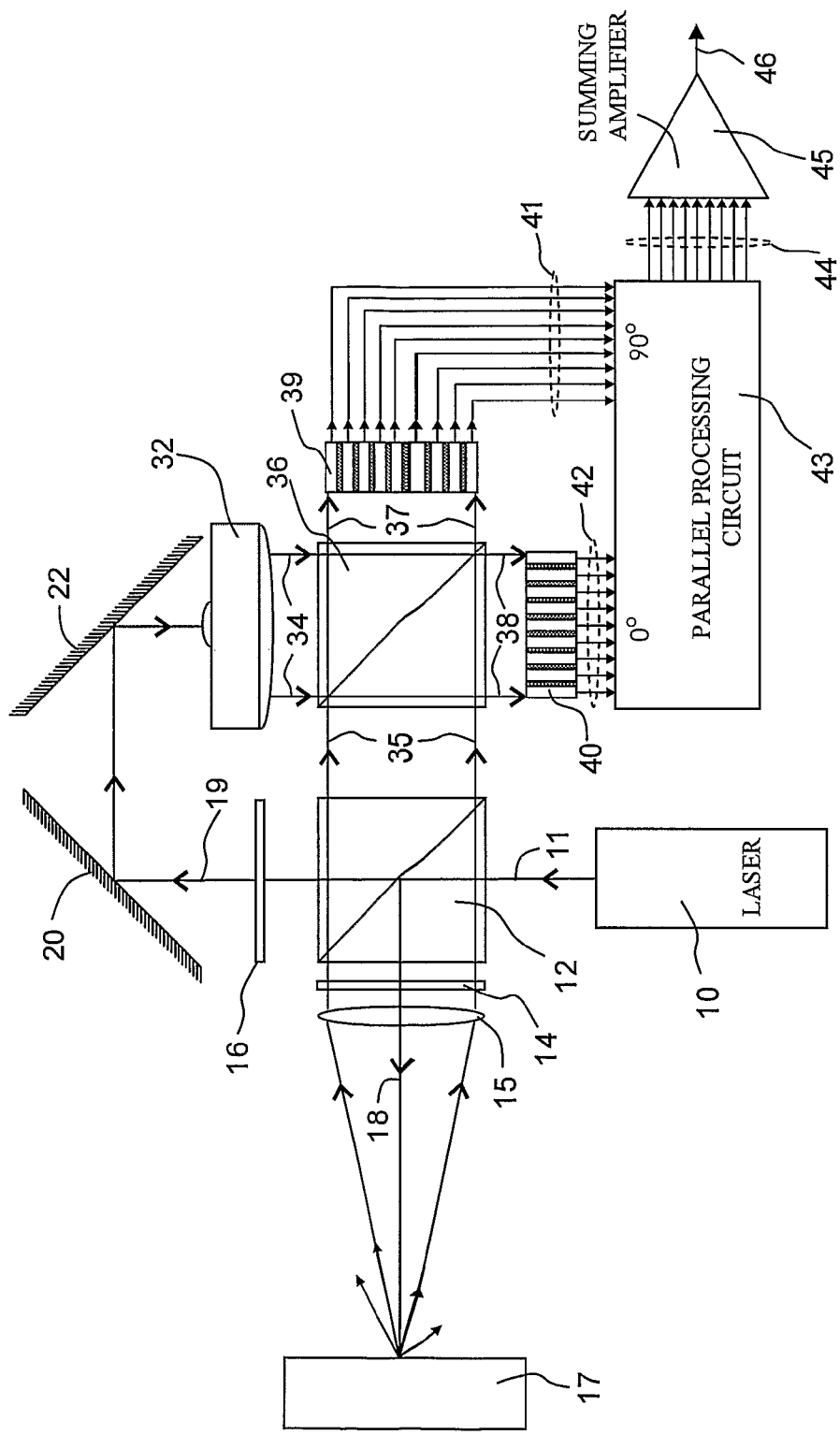
FIG. 2A is a schematic diagram of a multi-channel laser interferometric apparatus according to a first embodiment of the invention.

FIG. 2A illustrates a first preferred embodiment of the optical arrangement according to the invention. According to the invention, arrays of detectors 39 and 40 are used instead of single element detectors. These arrays may be linear arrays or two-dimensional arrays. Similarly to FIG. 1, the laser beam 11 is split in a probe beam 18 and a reference beam 19 using the beam splitter 12. As in the set-up of FIG. 1, the beam splitter 12 is a polarizing beam splitter. Non-polarizing beam splitter can be used, but polarization of laser beam must be aligned properly and polarizer must be added in the setup in order to clean the polarization of the scatter from the sample. The reference beam is expanded by the beam expander 32 such as to fully fill the active area of the array of detectors 39 and 40. The object beam 35, corresponding to the probe beam back-reflected by the workpiece and collected by the lens 15, is linearly polarized and is directed toward combining means 36. In the arrangement of FIG. 2A, the combining means comprise a polarizing beam splitter 36 for combining the linearly polarized scattered probe beam with the expanded circularly polarized reference beam 34 to obtain two optical fringe signals 37 and 38 having a phase shift of 90°. The optical fringe signals 37 and 38 are detected by the arrays of detectors 39 and 40. By using identical array of detectors that are positioned to look at the same optical fringe, then each pair of electrical fringe signals from the arrays of electrical fringe signals 41 and 42 corresponds to the same optical fringe and each pair exhibits a 90° phase difference between signals. The pair of quadrature signals defines a channel and each pair of signals is similarly processed by a parallel processing circuitry 43. The multiple processed signals 44 are then summed by a summing amplifier 45 in order to give an average output signal 46. The average output signal 46 can be proportional to displacement, velocity or displacement energy of the workpiece surface, depending on the processing scheme used for each channel, as it will be explained further in reference to FIGS. 5, 6, and 7.

Figure 2B:
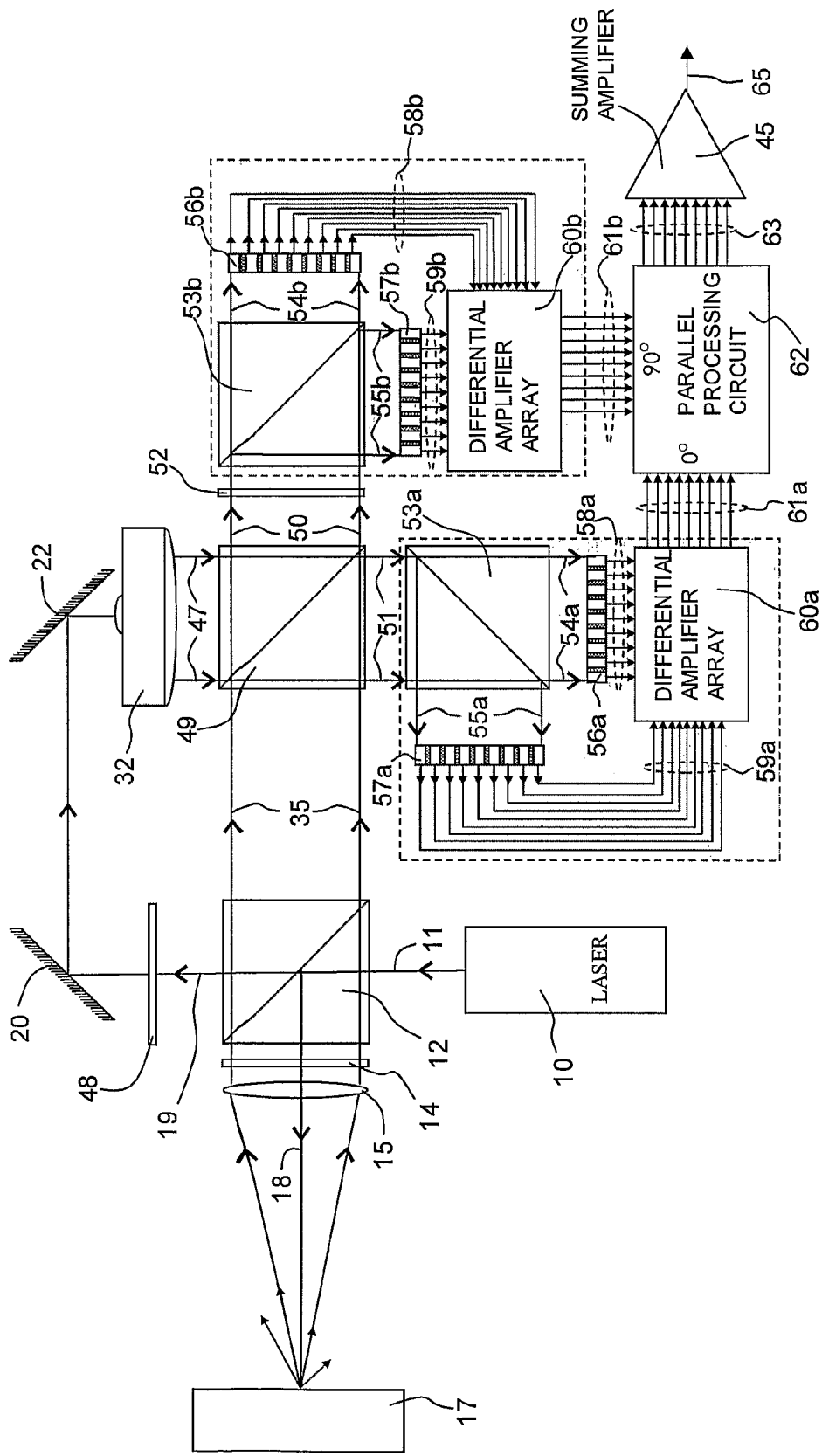
FIG. 2B is a variant of the embodiment shown in FIG. 2A which includes a differential detection scheme.

FIG. 2B illustrates a variant of the first embodiment shown in FIG. 2A which includes a differential detection scheme. The reference beam 19 passes through a half wave plate 48 whereby reference beam is linearly polarized and orthogonal to the object beam polarization 35. In this embodiment, the object beam 35 and the crossed polarized reference beam 47 are first divided by dividing means, as a beam splitter 49, into two optical signals 50 and 51. One of the optical signals, the optical signal 50 in FIG. 2B, passes through a quarter wave plate 52 which has its optical axis oriented along the polarization axis of the optical signal 50, resulting in a 90° phase shift between the two orthogonal polarizations. In this embodiment, the combining means comprise two polarizing beam splitters 53a and 53b and the receiving means comprise four arrays of detectors 56a, 56b, 57a and 57b. The partially transmitted object beam and reference beam 50 and 51 are made to interfere along the two polarization directions of the polarizing beam splitters 53a and 53b, respectively. The polarizing beam splitters 53a and 53b are oriented at 45° to the plane of the drawing. The resulting optical fringe signals along the two polarizations of the polarizing beam splitters phase 53a and 53b are received by the four arrays of detectors 56a, 56b, 57a and 57b. The four arrays of detectors 56a, 56b, 57a and 57b are identical, each set of four detectors of a corresponding channel generating two in-quadrature pairs (58a, 59a), (58b, 59b) of out-of-phase electrical signals. These signals 58a, 58b, 59a and 59b are sent to respective arrays of differential amplifiers 60a and 60b for subtracting each said out-of-phase electrical signals to obtain a pair of differential in-quadrature electrical signals 61a, 61b for each said channel, said pairs of differential in-quadrature electrical signals being processed together through the circuitry means 62. The multiple processed signals 63 are then summed by the summing amplifier 45 in order to give an average output signal 65. This optical arrangement uses a balanced detection scheme that is very advantageous when noisy lasers are used. With balanced detection, the common-mode noise that is identical for each detector is rejected by the subtraction process. Intensity noise from the laser is a source of common-mode noise and it can be effectively suppressed by the balancing, allowing the use of lower cost noisy laser without reduction in performance.

Figure 3:
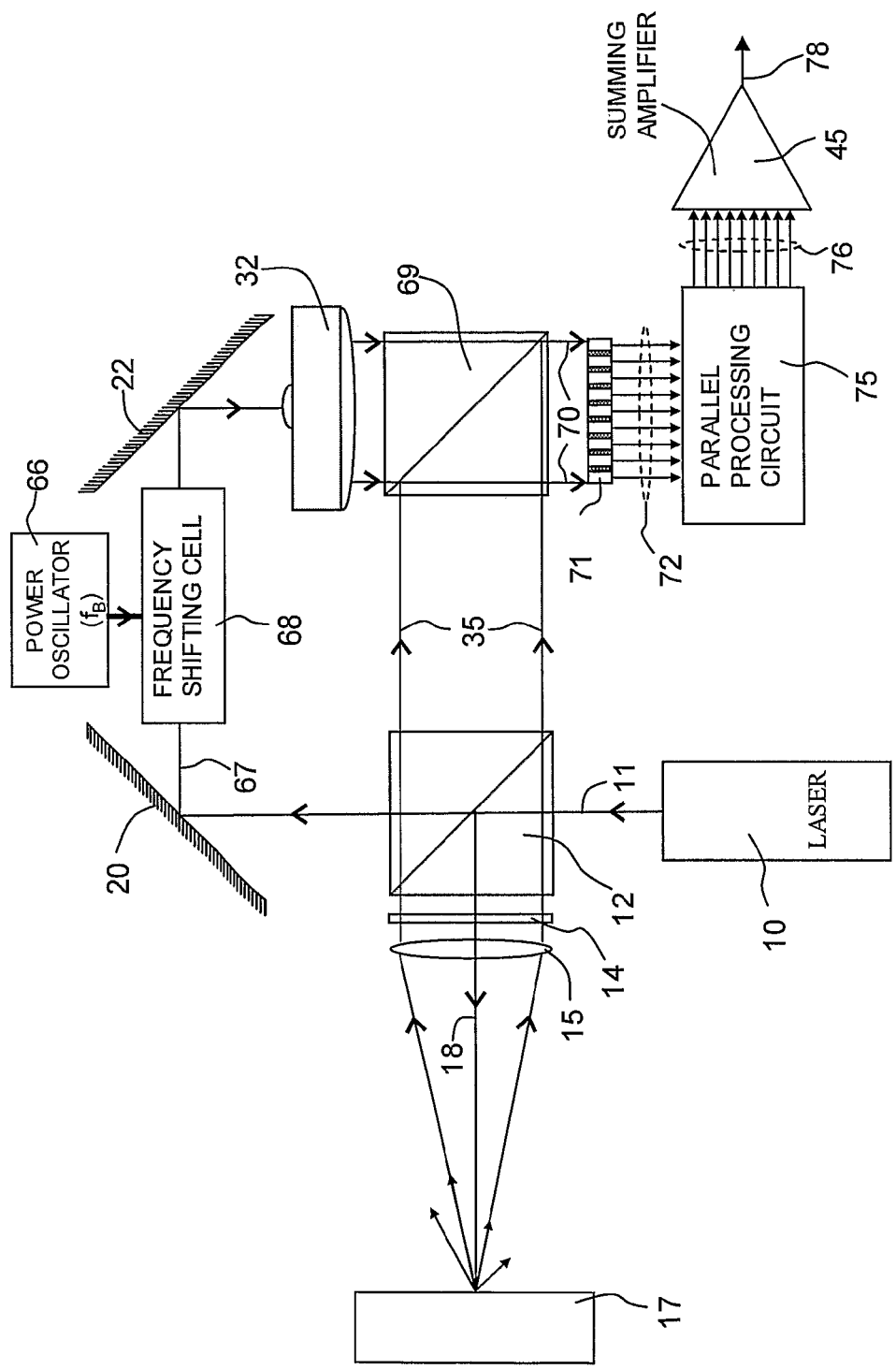
FIG. 3 is a schematic diagram of a second embodiment of a multi-channel laser interferometric apparatus which includes heterodyne modulation.

FIG. 3 illustrates a second embodiment according to the invention, in which the quadrature detection scheme is replaced by an heterodyne detection scheme. Similarly to FIG. 2, the laser beam 11 is split in a probe beam 18 and a reference beam 67. A frequency shifting device 68, such as a Bragg cell, is driven by a single frequency oscillator 66 producing a frequency shift at $f_B$ of the reference beam 67. After frequency shifting, the reference beam is expanded by the beam expander 32 such as to fully fill the active area of the array of detector 71. The linearly polarized object beam 35 and the linearly polarized frequency shifted reference beam 67 are mixed by the beam splitter 69 and the heterodyne optical fringe signal 70 is detected by the array of detector 71. The heterodyne signals 72 are processed by a parallel processing circuitry 75. The multiple processed signals 76 are then summed by a summing amplifier 45 in order to give an average output signal 78 proportional to displacement of the workpiece surface, as it will be detailed further, in reference to FIG. 10. This heterodyne scheme has the advantage of reducing the requirement on the laser quality in order to still achieve sensitive measurements. Indeed, the intensity noise spectrum of a laser generally exhibits much higher noise at lower frequency than at higher frequency. The noise spectrum often follows a 1/frequency dependency and with the heterodyne scheme, the frequency shifting effectively shifts the signal to higher frequency where the laser noise is lower. Compared to the balanced quadrature scheme, where intensity noise is rejected through balanced detection, this heterodyne scheme only requires a single detector array instead of four detector arrays as shown in FIG. 2B.

Figure 4A:
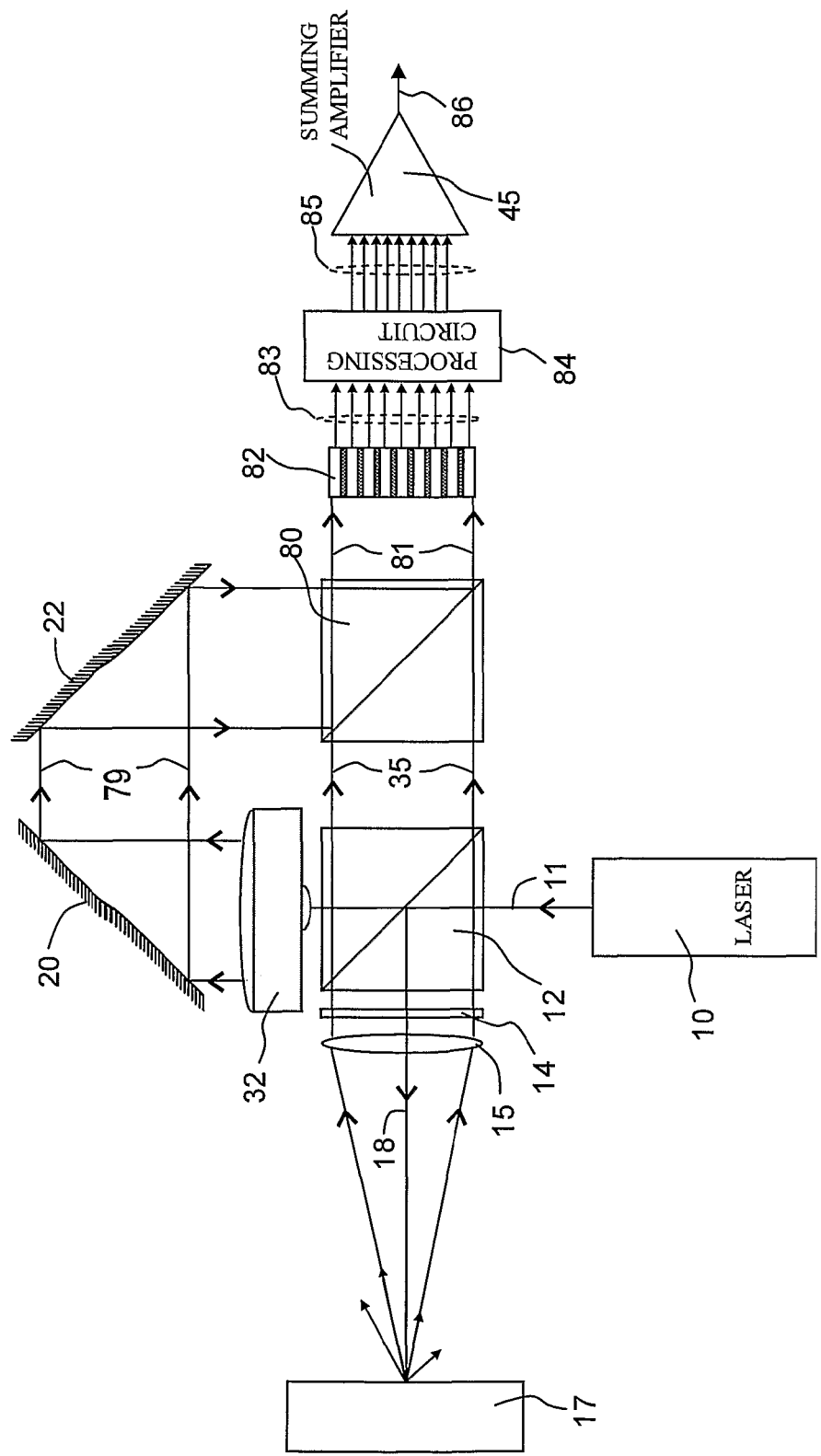
FIGS. 4A, 4B and 4C are schematic diagrams of a multi-channel laser interferometric apparatus according to other embodiments of the invention.

FIG. 4A illustrates a third preferred embodiment according to the invention, in which the quadrature detection scheme is performed statistically thanks to the random distribution of speckles. Similarly to FIG. 2, the laser beam 11 is split in a probe beam 18 and a reference beam 79. The reference beam is expanded by the beam expander 32 such as to fully fill the active area of the array of detector 82. The linearly polarized object beam 35 and the linearly polarized reference beam 79 are mixed by the beam splitter 80 and the optical fringe signal 81 is detected by the array of detector 82. The signals 83 are processed by a parallel processing circuitry 84. The multiple processed signals 85 are then summed by a summing amplifier 45 in order to give an average output signal 86 correlated to displacement of the workpiece surface. The parallel processing circuitry 84 process each signal independently and it can be based on either the square demodulation, as explained below in reference to FIG. 9A or the rectification demodulation, as explained below in reference to FIG. 9B. This embodiment minimizes the complexity of the system. Only a single detector array is needed and the critical alignment that was required with optical arrangements shown in FIG. 2A and FIG. 2B, in order to achieved quadrature between signal pairs, is no longer needed.

Figure 4B:
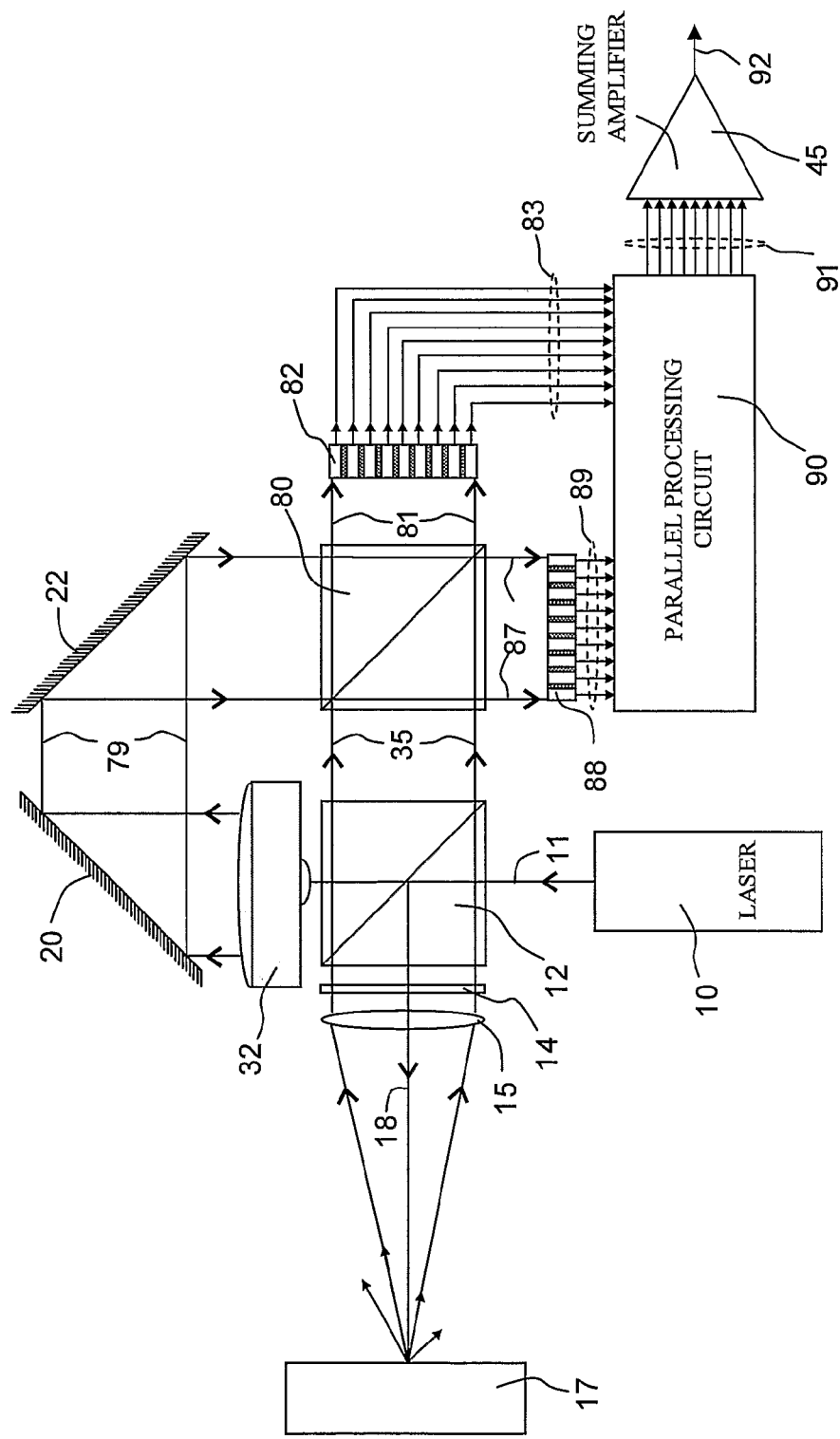

FIG. 4B illustrates a first variant of the third embodiment shown FIG. 4A which includes two arrays of detectors 82 and 88, making use of all the light available. Similarly to FIG. 4B, The linearly polarized object beam 35 and the linearly polarized reference beam 79 are mixed by the beam splitter 80. The optical fringe signals 81 and 87 are detected by the array of detectors 82 and 88. The signals 83 and 89 are processed by a parallel processing circuitry 90. In this embodiment the number of signals is doubled compared to the previous embodiment shown FIG. 4A. Similarly to the previous embodiment shown FIG. 4A, the parallel processing circuitry 90 process each signal independently and it can be based on either the square demodulation, as explained below in reference to FIG. 9A, or the rectification demodulation, as explained below in reference to FIG. 9B. Because each signal are processed independently, there is no accuracy requirement regarding the relative positioning of the arrays of detectors 82 and 88. The multiple processed signals 91 are then summed by a summing amplifier 45 in order to give an average output signal 92 correlated to displacement of the workpiece surface.

Figure 4C:
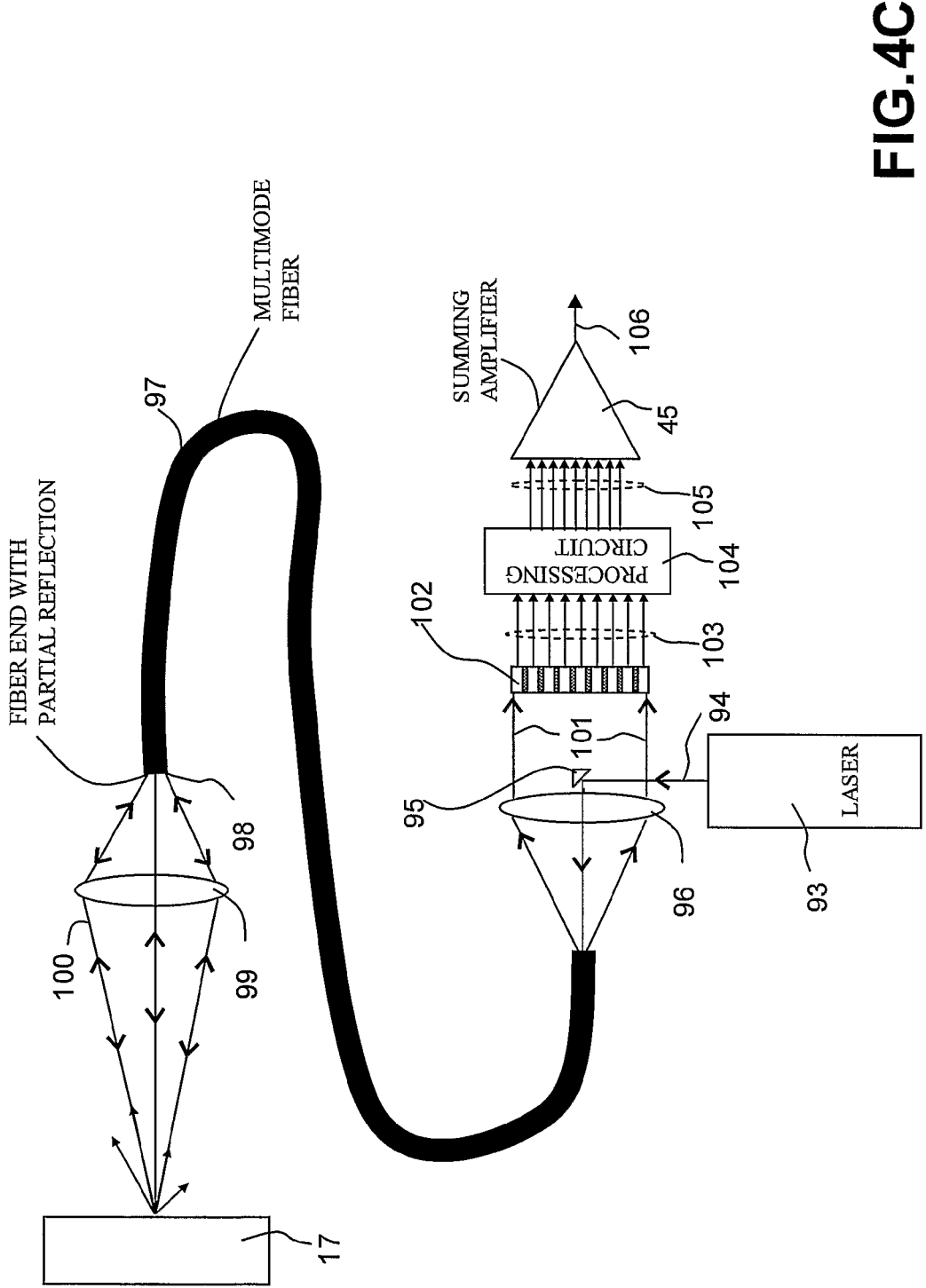

FIG. 4C illustrates a second variant of the third embodiment shown in FIG. 4A which uses a multimode fiber 97 to deliver the laser beam 94 onto the workpiece 17, to collect the scattered object beam 100 and to combine the reference beam and object beam for generating the optical fringe signal 101. A Cassegrain optical system composed of a small reflector 95, a turning prism or small mirror, and a large aperture lens is used to couple the laser beam 94 into the multi-mode fiber 97. The laser beam exiting the fiber end 98 is focused by mean of a lens 99 onto the surface of workpiece 17. The scattered object beam 100, is then focused back into the multi-mode fiber 97. A fraction of the laser beam is also back reflected by the partially reflective fiber end 98, generating the reference beam. The reference beam and the object beam are combined together during the back propagation in the multi-mode optical fiber 97. The optical fringe signal 101 exiting back the optical fiber is then focused by mean of the lens 96 onto the array of detectors 102. The signals 103 are then processed by a parallel processing circuitry 104 similarly to the embodiment described in FIG. 4A.

Figure 5:
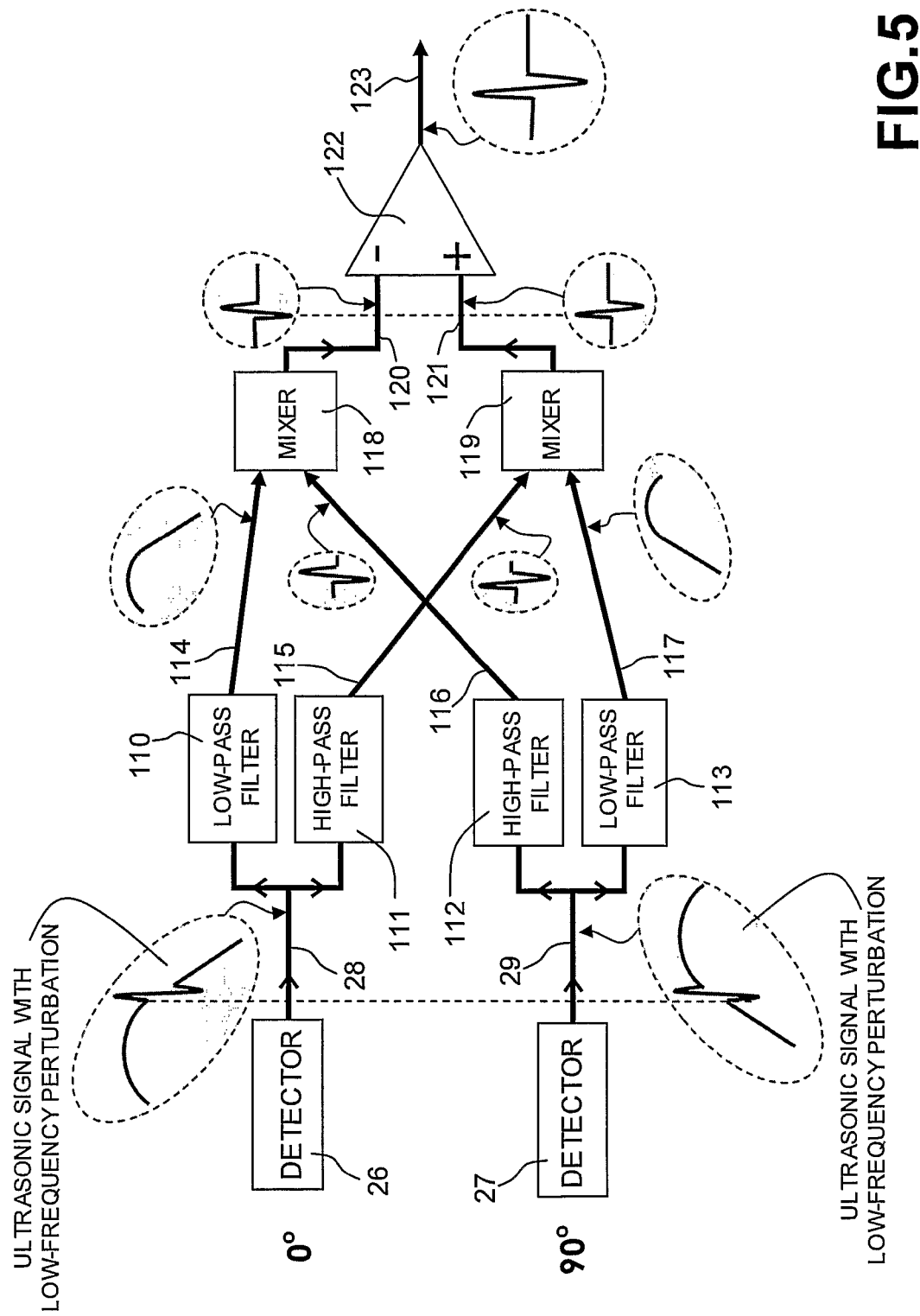
FIG. 5 is a schematic diagram of circuitry means for processing of signals in the embodiments shown in FIGS. 2A and 2B and for delivering an output signal proportional to displacement.
Figure 6:
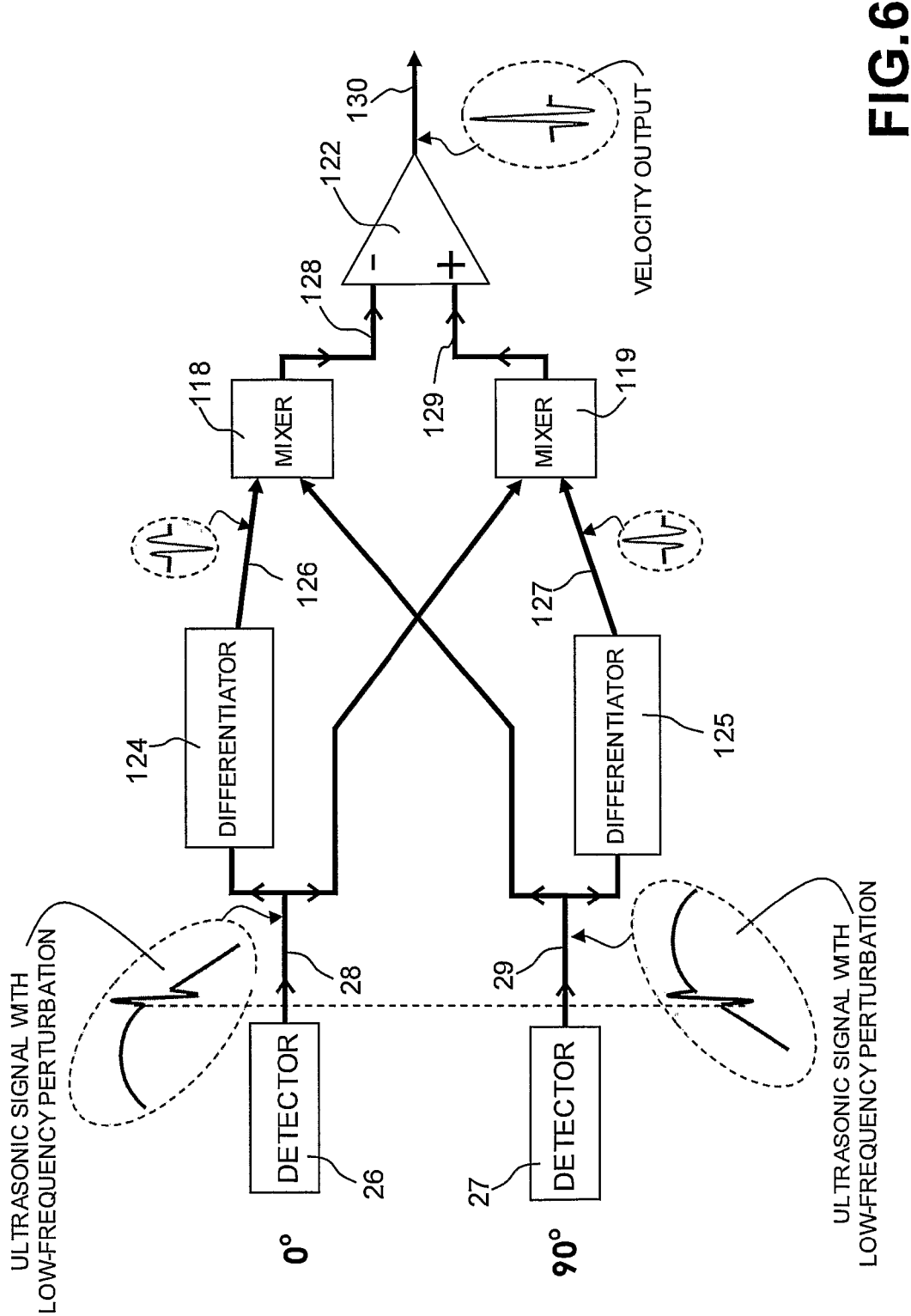
FIG. 6 is a schematic diagram of circuitry means for processing of signals in the embodiments shown in FIGS. 2A and 2B and for delivering an output signal proportional to velocity.
Figure 7:
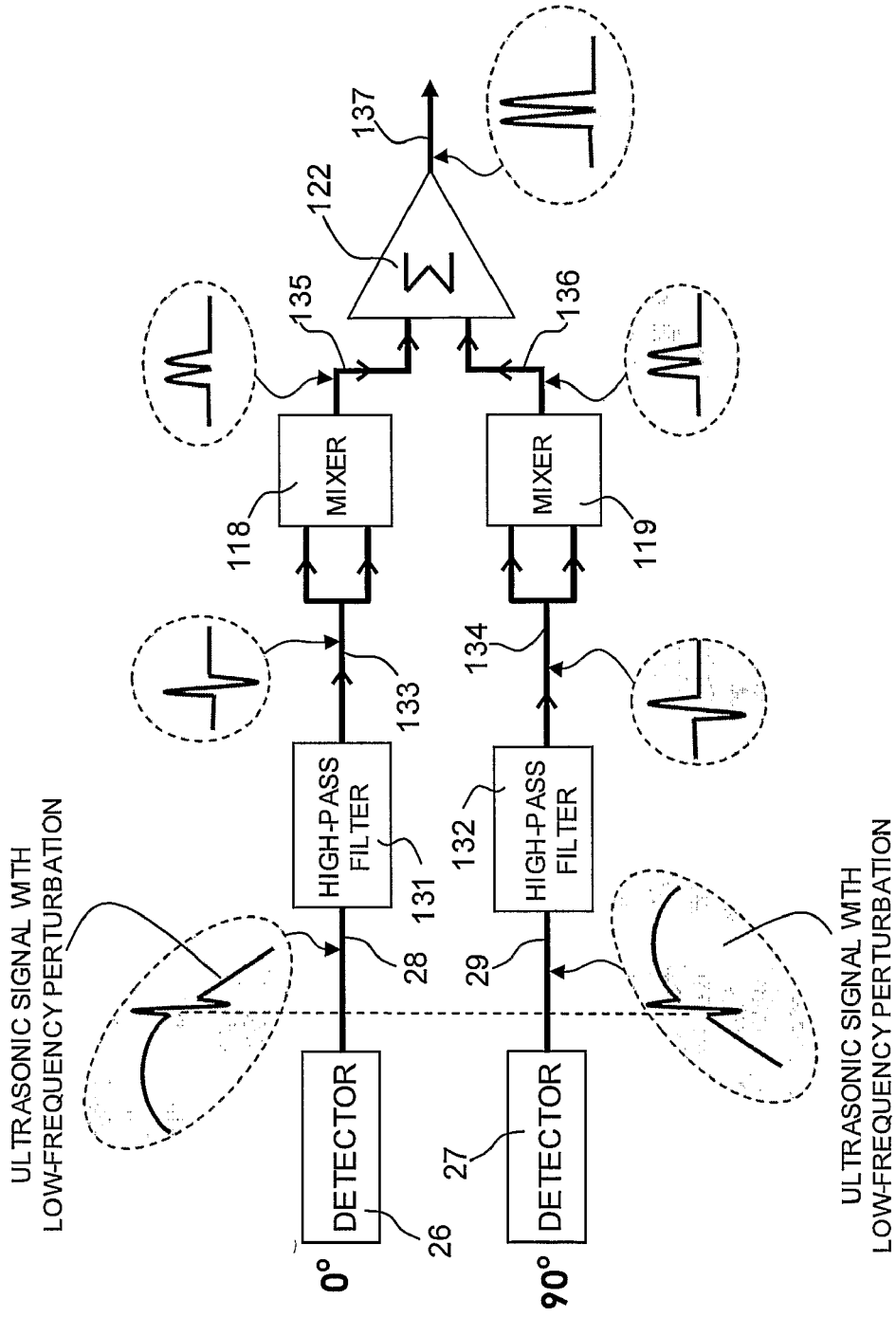
FIG. 7 is a schematic diagram of circuitry means for processing of signals in the embodiments shown in FIGS. 2A and 2B and for delivering an output signal proportional to displacement energy.

The processing circuit used for demodulation of quadrature signals is shown FIG. 5, FIG. 6 and FIG. 7. FIG. 5 describes a demodulation that gives an output signal proportional to the displacement. The two in-quadrature signals 28 and 29 generated by the detectors 26 and 27 are both divided into high frequency signals 115 and 116 and low-frequency two signals 114 and 117 using low-pass filters 110 and 113 and high-pass filter 111 and 112. Cross-multiplication by mixers 118 and 119 is then performed to generate two out-of-phase displacement signals 120 and 121. For instance, displacement signal 120 corresponds to the multiplication by mixer 118 between the high-frequency signal 116 of detector 27 and the low-frequency signal 114 of detector 26. Similarly, displacement signal 121 corresponds to the multiplication by mixer 119 between the high-frequency signal 115 of detector 26 and the low-frequency signal 117 of detector 27. The said two out-of-phase displacement signals 120 and 121 are then subtracted by the differential amplifier 122 to produce the output signal 123 proportional to the displacement of the workpiece surface.

By changing the nature of the filtering before cross multiplication, the output signal can also be made proportional to the velocity of the workpiece surface. This is shown on FIG. 6, where the in-quadrature signals 28 and 29 are both divided into the original signals and the derivative signals 126 and 127. Cross-multiplication by mixers 118 and 119 is then performed to generate two out-of-phase velocity signals 128 and 129. For instance, velocity signal 128 corresponds to the multiplication by mixer 118 between the derivative signal 126 of detector 26 and the signal 29 of detector 27. Similarly, velocity signal 129 corresponds to the multiplication by mixer 119 between the derivative signal 127 of detector 27 and the signal 28 of detector 26. The said two out-of-phase velocity signals 128 and 129 are then subtracted by the differential amplifier 122 to produce the output signal 130 proportional to the velocity of the workpiece surface.

A third demodulation scheme is shown in FIG. 7 where the mixers 118 and 119 are no longer used for cross-multiplication, but they are used instead for squaring the high-frequency signals 133 and 134. The two in-quadrature signals 28 and 29 generated by the detectors 26 and 27 are filtered to remove their low frequency components by the high-pass filters 131 and 132. the filtered signals 133 and 134 are then squared by mixer 118 and 119. The two squared signals 135 and 136 are then added into a summing amplifier 122 to produce the output signal proportional to the displacement energy 137, the square of the displacement, of the workpiece surface.

Figure 8:
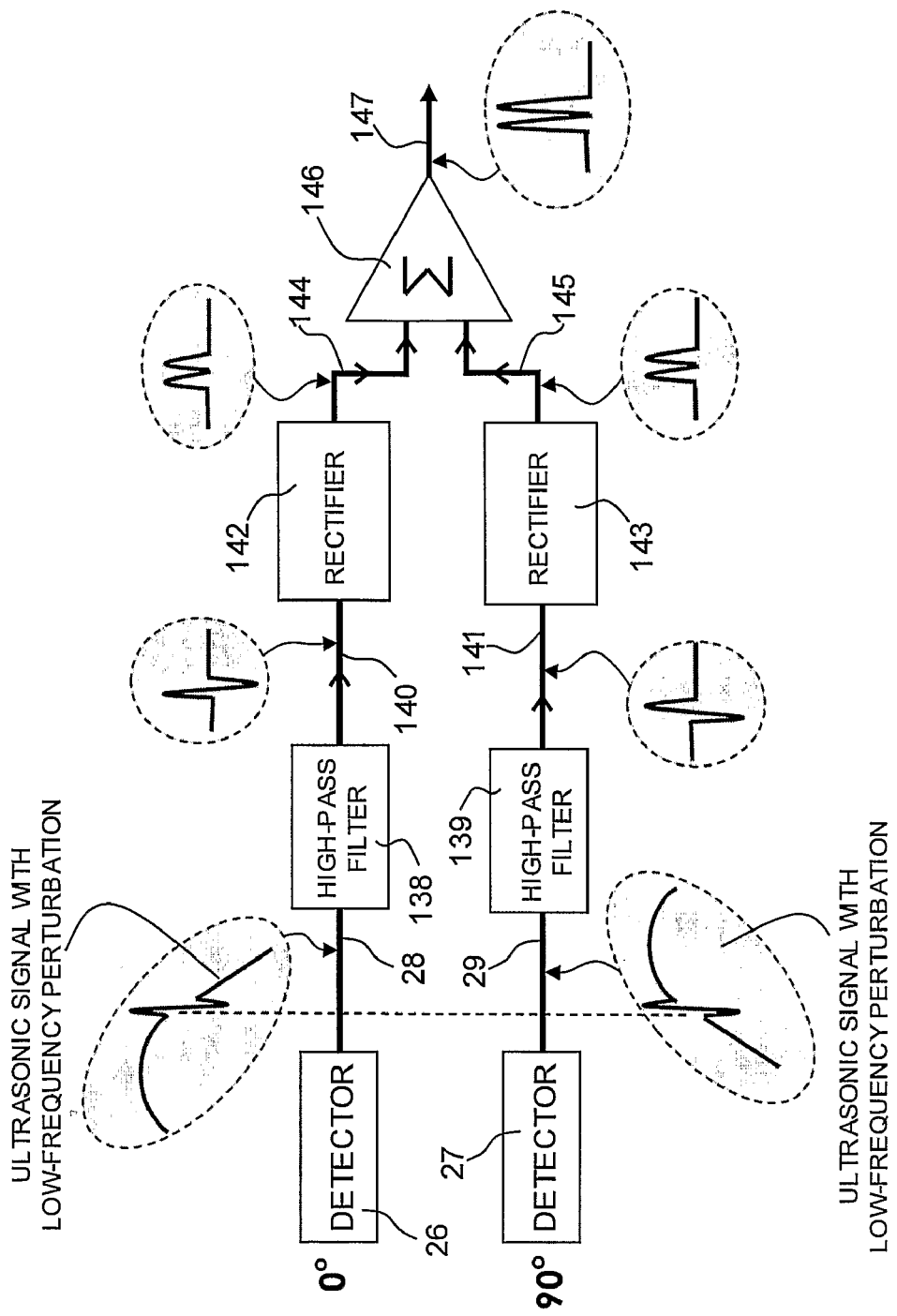
FIG. 8 is a schematic diagram of a variant of the signal processing shown in FIG. 7 which delivers an output signal correlated to displacement.

The three quadrature demodulations described in FIG. 5, FIG. 6 and FIG. 7 lead to an output signal that is independent of the absolute phase of the optical fringe signals. The only requirement for stable, phase-independent signal is to have two in-quadrature signals. A variant of the demodulation scheme shown FIG. 7 is shown in FIG. 8. In FIG. 8, the squaring of the filtered signals is now replaced by a rectification of the filtered signals. The in-quadrature signals 28 and 29 are both filtered with high-pass filters 138 and 139. The high-frequency signals 140 and 141 are then rectified using rectifiers 142 and 143. The two rectified signals 144 and 145 are then added by a summing amplifier 146 to produce the output signal 147 correlated to the absolute value of the displacement of the workpiece surface. With this demodulation scheme, the amplitude of the output signal 146 varies between 100% and 140% of its true value depending on the phase of the optical fringe signal. The use of rectification instead of multiplication gives a less accurate measurement, but it is simpler to implement electronically, and can be well adapted to some kinds of applications.

Figure 9A:
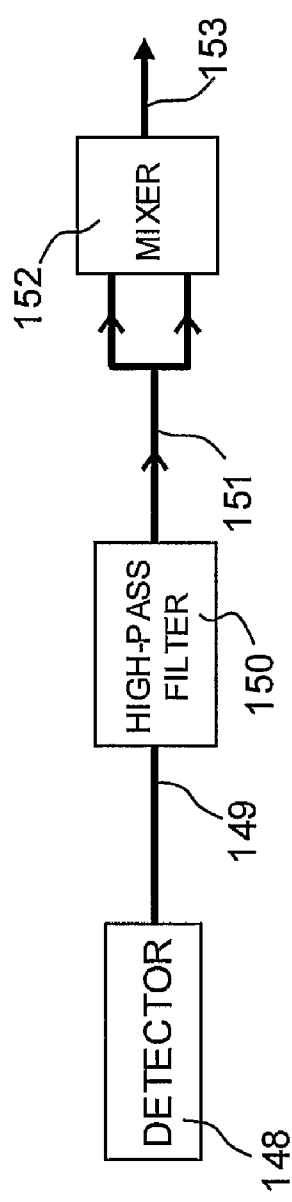
FIGS. 9A and 9B are schematic diagrams of circuitry means for processing of signals in the embodiments shown in FIGS. 4A, 4B and 4C and for delivering an output signal correlated to displacement.
Figure 9B:
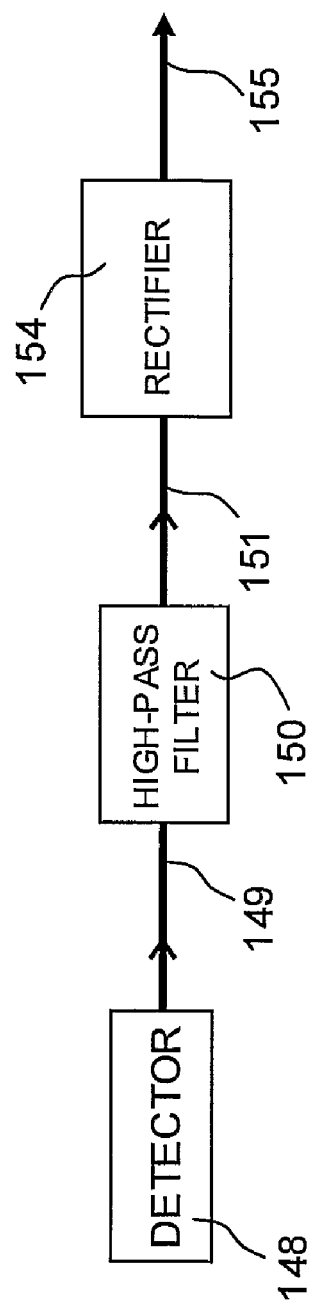

For the embodiments according to the invention described in FIG. 4A, FIG. 4B and FIG. 4C, in which the quadrature detection scheme is based on the random distribution of speckle. The demodulation carried out by the processing circuit is described in FIG. 9A and FIG. 9B. Here, single channel processing, not requiring cross-multiplication, is performed instead because in-quadrature signals are not available for these embodiments. The signal 149 from detector 148 is first filtered using a high-pass filter 150 and the high-frequency signal 151 is then either squared using mixer 152 as shown in FIG. 9A or rectified using rectifier 154 shown in FIG. 9B.

Figure 10:
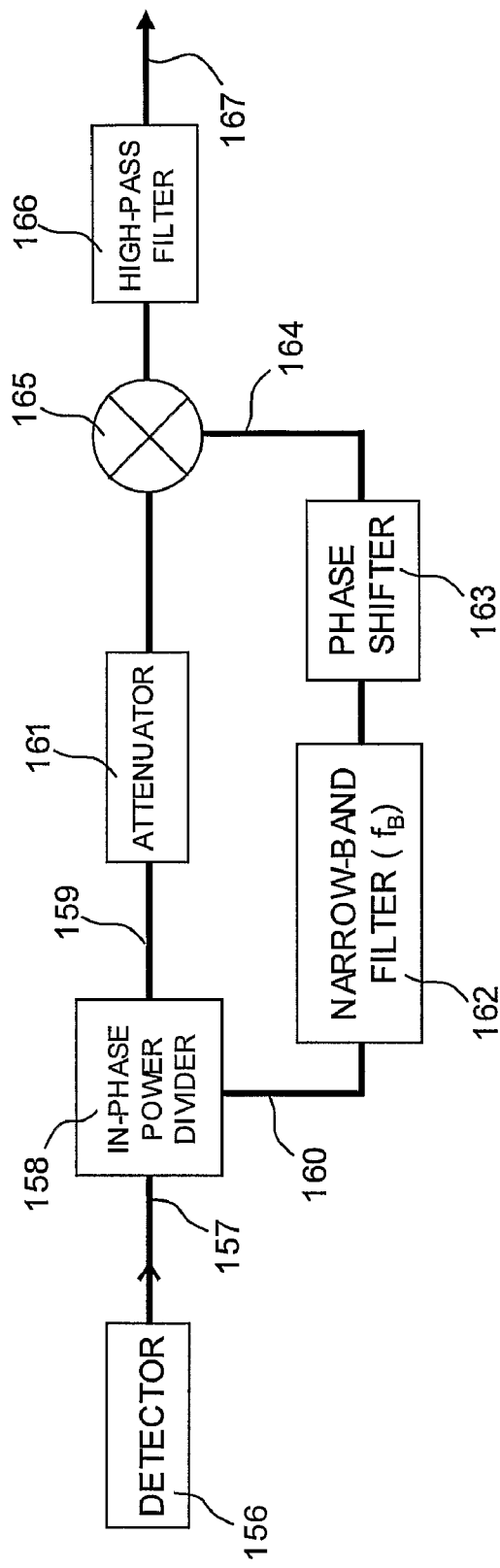
FIG. 10 is a schematic diagram of circuitry means for processing of signals in the embodiments shown in FIG. 3 and for delivering an output signal proportional to displacement.

Finally, for the embodiment described in FIG. 3, where heterodyne detection scheme is used, the processing circuit is described in FIG. 10. The heterodyne signal 157 is divided in two in-phase signals 159 and 160 by in-phase power divider 158. The signal component 160 is first filtered by means of narrow-band filter 162 which rejects the sidebands, i.e. the ultrasonic signal modulation, and only keeps the carrier signal at frequency $f_B$. The carrier signal 164 is then delayed by phase shifter 163. The value of the phase shift is adjusted such that the phase difference between the two signals 159 and 164 sent to the mixer 165 equals 90°. The signal component 159 is sent to the one of the port of the mixer 165 after being attenuated by attenuator 161 in order to match the amplitude of the carrier signal 164 that is sent to the other port of the mixer 165. After the mixer, the low-pass filter 166 removes the signal components at $2*f_B$ that was generated by the mixing process in order to only keep the low-frequency component of the signal 167 and corresponding to the ultrasonic displacement of workpiece surface.

The invention claimed is:

1. A multi-channel laser interferometric method for measuring the displacement of a surface of a material subjected to ultrasound, which comprises:
   generating a laser beam having a predetermined intensity;
   dividing the laser beam into a reference beam and a probe beam having respective intensities representing minor and major fractions of the predetermined intensity;

passing the probe beam through an optical lens to focalize the probe beam onto the surface of the material subjected to ultrasound, thereby scattering same;

expanding the reference beam;

combining the scattered probe beam collected by said optical lens with said expanded reference beam to obtain an optical fringe signal;

receiving said optical fringe signal on at least one array of photodetectors, wherein said optical fringe signal fully covers said array and each photodetector of the array defines a channel, having a given aperture smaller than the aperture of said optical lens to receive a portion of said optical fringe signal and converting said portion of said optical fringe signal into an electrical signal;

processing for each channel said electrical signals through circuitry means;

summing electrically said processed signals to extract an output signal correlated to the motion of said surface.

2. A method according to claim 1, wherein processing comprises first filtering said signals, then squaring said filtered signals.

3. A method according to claim 1, wherein processing comprises first filtering said signals, then rectifying said filtered signals.

4. A method according to claim 1, wherein it further comprises:

linearly polarizing the scattered probe beam collected by the optical lens, circularly polarizing the expanded reference beam;

combining the linearly polarized scattered probe beam with the circularly polarized expanded reference beam to obtain two optical fringe signals having a phase shift of 90[deg.];

receiving the first and second optical fringe signals on two arrays of detectors, the two arrays of detectors being identical, two detectors of the corresponding channels of the arrays generating two in-quadrature electrical signals, the electrical signal pairs being then processed together through said circuitry means.

5. A method according to claim 4, wherein the step of processing comprises:

first dividing and filtering said in-quadrature signal pairs to separate each signal into a high-frequency signal and a low-frequency signal, then for each signal pair, Generating two signals by cross-multiplication between the said low-frequency signal pair and the said high-frequency signal pair, differentiating the said two signals.

6. A method according to claim 4, wherein the step of processing comprises:

first dividing and processing said in-quadrature signal pairs to separate each signal into the original signal and its derivative signal, then for each signal pair, Generating two signals by cross-multiplication between the said original signal pair and the said derivative signal pair, differentiating the said two signals.

7. A method according to claim 4, wherein the step of processing comprises:

first high-pass filtering said signal pairs, then for each signal pair, summing the two signals obtained by squaring of each signal of the signal pair.

8. A method according to claim 4, wherein the step of processing comprises:

first high-pass filtering said signal pairs, then for each signal pair, summing the two signals obtained by rectification of each signal of the signal pair.

9. A method as claimed in claim 1, wherein said scattered probe beam and said expanded reference beam having crossed polarization, it further comprises dividing each of the scattered probe beam and the expanded reference beam in two optical signals having a 180[deg.] phase difference, the combining of the optical signals resulting in four optical fringe signals having −90[deg.], 0[deg.], 90[deg.] and 180[deg.] relative phase differences; and wherein the step of receiving further comprises:

receiving the four optical fringe signals on four arrays of detectors, the four arrays of detectors being identical, each set of four detectors of a corresponding channel generating two in-quadrature pairs of out-of-phase electrical signals, subtracting each said out-of-phase electrical signals to obtain a pair of differential in-quadrature electrical signals for each said channel, said pairs of differential in-quadrature electrical signals being processed together through said circuitry means.

10. A method as claimed in claim 1, wherein it further comprises:

frequency shifting said reference beam, the optical fringe signal resulting from combining said scattered probe beam with said expanded shifted reference beam being an heterodyne optical fringe signal, and the step of processing comprising demodulating each electrical signal for each channel by removing the frequency shift using heterodyne demodulation techniques.

11. A multi-channel laser interferometric apparatus for measuring the motion of a surface of a material subjected to ultrasound, which comprises:

a laser source for generating a laser beam having a predetermined intensity;

a beam splitter for dividing said laser beam into a reference beam and a probe beam having respective intensities representing minor and major fractions of said predetermined intensity;

an optical lens disposed for focalizing said probe beam onto the surface of said material subjected to ultrasound, thereby scattering same;

a beam expander expanding said reference beam;

combining means for combining the scattered probe beam with said expanded reference beam to obtain an optical fringe signal;

receiving means with at least one array of detectors for receiving said optical fringe signal on, wherein the optical fringe signal fully covers the array, and each detector, defining a channel, has a given aperture smaller than the aperture of said optical lens to receive a portion of said optical fringe signal and convert said portion of said optical fringe signal into an electrical signal;

circuitry means for processing for each channel said electrical signals and summing said processed signals to extract an output signal correlated to motion of the surface.

12. An apparatus according to claim 11, wherein circuitry means comprise filtering means for filtering the electrical signals and squaring means for squaring the filtered signals.

13. An apparatus according to claim 11, wherein circuitry means comprise filtering means for filtering the electrical signals and rectifying means for rectifying the filtered signals.

14. An apparatus according to claim 11 further comprising polarizing means for circularly polarizing the expanded reference beam, wherein:

the combining means comprise a polarizing beam splitter for combining the linearly polarized scattered probe beam with the expanded circularly polarized reference beam to obtain two optical fringe signals having a phase shift of 90[deg.];

the receiving means comprise two identical arrays of detectors for receiving the optical fringe signals on, the two detectors of a same channel of each array generating a pair of in-quadrature electrical signals, the pairs of in-quadrature electrical signals being then processed together by the circuitry means.

15. An apparatus according to claim 11, wherein it further comprises:

polarizing means for setting the polarization of the expanded reference beam orthogonal to the polarization of the probe beam;

dividing means to divide each of the polarized scattered probe beam and the expanded orthogonally polarized reference beam into a first and a second signals;

an optical retardation device in one of the first or second optical signals to obtain a phase shift of 90[deg.] between the first and second optical signals; and wherein:

the combining means comprise two polarized beam splitters for combining the two orthogonally polarized components of the first and second optical signals, each into two optical fringe signals having a 180[deg.] phase difference; resulting in four optical fringe signals having −90[deg.], 0[deg.], 90[deg.] and 180[deg.] relative phase differences;

the receiving means comprise four identical arrays of detectors for receiving the four optical fringe signals, each set of four detectors of a corresponding channel generating two pairs of out-of-phase electrical signals, the circuitry means further comprise subtracting means for subtracting each of the out-of-phase electrical signals to obtain a pair of differential in-quadrature electrical signals for each said channel, the pairs of differential in-quadrature electrical signals being then processed together.

16. A multi-channel laser heterodyne interferometric apparatus according to claim 11, wherein it further comprises a frequency shifting device for frequency shifting the reference beam by a given frequency, the frequency shifted reference being then expended, and wherein:

the combining means combine the scattered probe beam with the expanded frequency shifted reference beam to obtain an heterodyne optical fringe signal, the heterodyne optical fringe signal being received by the receiving means;

the circuitry means comprise demodulation means for processing for each channel the heterodyne electrical signals through demodulation by removing the frequency shift using standard heterodyne demodulation techniques, the output signal obtained by summing the processed signals being proportional to the displacement of the surface.

17. An apparatus according to claim 11, wherein the array of detectors is a linear array of detectors.

18. An apparatus according to claim 11, wherein the array of detectors is a two-dimensional array of detectors.

19. A multi-channel fiberized laser interferometric apparatus according to claim 11, wherein it further comprises a multi-mode optical fiber and coupling means for coupling the laser beam into the optical fiber, and wherein:

a partially reflecting coating at the optical fiber end enables dividing the laser beam into the reference beam and the probe beam;

the optical lens for focalizing the probe beam onto the surface of the material is disposed at the end of the optical fiber, and refocuses the scattered probe beam into the optical fiber;

the receiving means comprise at least one two-dimensional array of detectors and a second optical lens for focusing on the array of detectors the multi-mode optical beam exiting though the entrance face of the multi-mode fiber and corresponding to the mixing between the scattered beam and the partially reflected beam.

20. A laser interferometric apparatus for measuring a displacement of an object, the apparatus comprising:

a laser source for producing a laser beam having a given intensity;

a beam splitter for dividing the laser beam into a reference beam and an object beam to be directed to the object, thereby producing a scattered object beam being modulated according to the displacement of the object;

a beam combiner for combining the scattered object beam and the reference beam to provide at least one interference beam;

at least one array of detectors for receiving the at least one interference beam, each detector of the array receiving a portion of the at least one interference beam to form an electrical interference signal, the electrical interference signal comprising a wanted signal component indicative of the object displacement and a substantially equal intensity noise component; and a processing circuit comprising a differential amplifier for subtracting at least two electrical interference signals formed by at least two portions of the interference beam, thereby generating a displacement signal, the displacement signal comprising substantially the wanted signal component alone, wherein the intensity noise is substantially rejected.

21. A method for measuring a displacement of an object, the method comprising:

generating a laser beam having a given intensity;

dividing the laser beam into a reference beam and an object beam to be directed to the object, thereby producing a scattered object beam being modulated according to the displacement of the object;

combining the scattered object beam and the reference beam to provide at least one interference beam;

receiving the at least one interference beam with at least one array of detectors, each detector array receiving a portion of the at least one interference beam to form an electrical interference signal, the electrical interference signal comprising a wanted signal component indicative of the object displacement and a substantially equal intensity noise component; and processing at least two electrical interference signals formed by at least two portions of the interference beam, the processing comprising subtracting the at least two electrical interference signals, thereby generating an output signal, the output signal comprising substantially the wanted signal component alone, wherein the intensity noise is substantially rejected.

* * * * *